United States Patent [19]
Gallucci et al.

[11] Patent Number: 5,596,049
[45] Date of Patent: Jan. 21, 1997

[54] STABILIZATION OF POLYESTERS USING EPOXY COMPOUNDS IN COMBINATION WITH A CATALYST

[75] Inventors: Robert R. Gallucci, Mt. Vernon; Linda H. Nelson; Thomas G. Shannon, both of Evansville, all of Ind.

[73] Assignee: General Electric Company, Pittsfield, Mass.

[21] Appl. No.: 479,232

[22] Filed: Jun. 7, 1995

Related U.S. Application Data

[63] Continuation of Ser. No. 160,993, Dec. 2, 1993, abandoned, which is a continuation of Ser. No. 987,588, Dec. 8, 1992, abandoned, which is a continuation of Ser. No. 732,188, Jul. 18, 1991, abandoned.

[51] Int. Cl.$^6$ ........................................... C08F 20/00
[52] U.S. Cl. .................... 525/438; 525/530; 525/533; 428/413; 428/480; 428/482
[58] Field of Search ...................... 525/438, 530, 525/533; 428/413, 480, 482

[56] References Cited

U.S. PATENT DOCUMENTS

| | | | |
|---|---|---|---|
| 3,886,104 | 5/1975 | Borman et al. | 260/22 |
| 4,020,122 | 4/1977 | Borman et al. | 260/835 |
| 4,071,504 | 1/1978 | Korver | 260/75 |
| 4,130,541 | 12/1978 | Lazarus et al. | 260/45.8 |
| 4,141,882 | 2/1979 | Kodama et al. | 260/40 |
| 4,229,553 | 10/1980 | Sterzel et al. | 525/438 |
| 4,246,378 | 1/1981 | Kometani et al. | 525/438 |
| 4,276,208 | 6/1981 | Ogawa et al. | 523/456 |
| 4,533,679 | 8/1985 | Rawlings | 523/204 |
| 4,540,729 | 9/1985 | Williams | 525/411 |
| 4,753,975 | 6/1988 | Vanderkooi, Jr. | 525/438 |
| 4,758,636 | 7/1988 | Hijikata et al. | 525/438 |
| 4,795,771 | 1/1989 | Yoshihara | 524/114 |
| 4,892,901 | 1/1990 | Liu | 524/303 |
| 4,904,746 | 2/1990 | Brown et al. | 525/438 |
| 4,933,429 | 6/1990 | McCracken et al. | 528/272 |
| 4,999,388 | 3/1991 | Okamoto | 525/438 |

FOREIGN PATENT DOCUMENTS 2098231  11/1982  United Kingdom .

OTHER PUBLICATIONS

"Encyclopedia of Science and Technology", vol. 6, pp. 322–382. 1986.

*Primary Examiner*—Melvyn I. Marquis
*Assistant Examiner*—Randy Gulakowski

[57] ABSTRACT

A novel polyester composition is disclosed comprising a linear polyester resin, a difunctional epoxy compound and a catalyst. The novel polyester compositions have excellent melt viscosity properties including excellent retention of melt viscosity after aging.

39 Claims, No Drawings

STABILIZATION OF POLYESTERS USING EPOXY COMPOUNDS IN COMBINATION WITH A CATALYST

CROSS REFERENCE TO RELATED APPLICATIONS

This is a Ser. No. 08/160,993 filed on Dec. 02, 1993 now abandoned which is a continuation of 07/987,588 filed Dec. 08, 1992 now abandoned which is a continuation of 07/732,188 filed Jul. 18, 1991 now abandoned.

FIELD OF INVENTION

The present invention relates to polyester compositions. More particularly the present invention relates to polyester compositions having improved hydrolytic stability and melt viscosity stability. Most particularly, the present invention relates to linear polyester resins stabilized with epoxy compounds in combination with a catalyst.

BACKGROUND OF THE INVENTION

Linear polyesters, such as poly(ethylene terephthalate) or PET, and poly(butylene terephthalate) or PBT, are widely used in the preparation of articles by forming methods such as injection molding and tube extrusion. Many of their properties, including chemical stability, solvent resistance and low permeability to gases, make them attractive candidates for such forming operations as blow molding, profile extrusion and thermoforming. One problem in such operations is the relatively low melt viscosities of the polyesters, as a result of which the formed articles do not adequately retain their shape immediately after forming and before they have cooled.

In recent years, various methods have been developed for increasing the melt viscosities and melt strengths of such polyesters.

Kodama et al., U.S. Pat. No. 4,141,882, describe obtaining a polyester composition having high melt viscosity by blending a polyester comprising at least 80 mole percent of ethylene terephthalate units with (1) an epoxy compound of isocyanuric acid construction (A) and at least one organic compound (B) capable of reacting with the epoxy compound (A), or (2) a product of the melt reaction of epoxy compound (A) with the organic compound (B).

Blaschke et al., United Kingdom Patent No. 2,098,231 describe shaped bodies formed of polytetramethylene terephthalate stabilized with triglycidyl isocyanurate (TGIC) or a bisoxazoline.

Yosihara, U.S. Pat. No. 4,795,771, describes polyesters exhibiting crystallization at low temperatures and having high heat distortion temperatures and good dimensional stability. The disclosed polyester compositions consist of polyester, of which 80% is poly(ethylene terephthalate), a carboxylic acid ester of a polyalkylene glycol, an epoxy compound having a polyoxyalkylene and an inorganic filler such as talc.

Rawlings, U.S. Pat. No. 533,679, describes reinforced polyesters consisting of a polyester resin, a polyepoxy having more than two epoxide functionalities and a reinforcing agent.

Borman et al., U.S. Pat. No. 4,020,122, describe a method to increase the melt elasticity or viscosity of linear high molecular weight polyesters. The patentees teach adding to the polyester organic polyepoxides having at least two epoxide groups per molecule.

Korver, U.S. Pat. No. 4,071,504, disclose low carboxyl content polyester fibers. The fibers are produced by melt extruding a polyester and a catalytic material, such as an alkali metal salt, and adding and reacting therewith monofunctional epoxies.

Brown et al., U.S. Pat. No. 4,904,746, teach producing branched polyesters having advantageous melt viscosity properties. The improved method comprises forming a reactive concentrate by reacting (A) triglycidyl isocyanurate with (B) a linear polymer having ester and free carboxylic groups. The reactive concentrate is then melt blended with (C) a linear polyester with free carboxylic groups.

McCracken et al., U.S. Pat. No. 4,933,429, teach the production of high melt viscosity branched polyesters. The disclosed branched polyesters are produced by effecting a reaction between (A) a polyester having a substantial portion of free carboxylic groups, (B) a polyepoxy compound, preferably having at least three epoxy functionalities, and (C) a catalyst selected from salts of aliphatic carboxylic acids and primary alkylamines.

Kometani et al., U.S. Pat. No. 4,246,378, further describe a polyester having improved melt stability. The patentees teach preparing a composition having 100 parts by weight of polyester, 0.1–40 parts by weight of an epoxy compound, and 0.001–10 parts by weight of organic sulfonate salts and organic sulfate salts.

Borman et al., U.S. Pat. No. 3,886,104, teaches stabilizing high molecular weight polyester resins by adding to the polyester resin a stabilizer comprising an internally polyfunctional epoxide having at least two epoxide functionalities. The epoxide containing stabilizers disclosed to be useful are epoxidized polyunsaturated triglycerides.

Commonly assigned U.S. patent application Ser. No. 07/526,579, filed May 17, 1990 now abandoned discloses branched polyesters having enhanced melt viscosity. The application describes adding a reinforcing mineral to a polyester resin branched with a TGIC branching agent.

However, the above-described polyester compositions still suffer from processing drawbacks at high melt viscosities. This processability difficulty resulted from melt stiffness encountered when larger amounts of polyepoxide functional agents were employed. Thus, there exists in the art a need for high melt viscosity linear polyester resins which are easily processable.

Surprisingly, it has now been found that compositions comprising linear polyesters, difunctional epoxides and salts of aliphatic carboxylic acids provide a composition which possesses both excellent hydrolytic stability and melt viscosity stability. Further, preferred polyester compositions possess high melt viscosity and ease of processability. The compositions of the present invention unexpectedly exhibit improved results over compositions employing mono- and tri-functional epoxides.

It is further noteworthy that while compositions containing linear polyesters and branched polyesters have good hydrolytic stability, surprisingly the linear polyester compositions of the present invention are better than the branched in this respect.

SUMMARY OF THE INVENTION

According to the present invention there is provided a thermoplastic resin composition comprising (a) a linear polyester resin; (b) a difunctional polyepoxy compound; and (c) a catalyst. Preferably the compositions of the present invention further comprises (d) a hindered phenol antioxidant.

Preferably the polyester component (a) is selected from the group consisting of poly(1,4-butylene terephthalate), poly(ethylene terephthalate), poly(1,4-cyclohexanedimethanol terephthalate) and blends of any of the foregoing, and is present in an amount ranging from about 60 to about 100 weight percent based on the weight of the total composition.

The preferred difunctional polyepoxy compound (b) is 3,4-epoxycyclohexylmethyl-3,4-epoxycyclohexylcarboxylate. The preferred catalysts (c) are salts of an aliphatic carboxylic acid. The most preferred catalyst (c) is sodium stearate.

Also according to the present invention there is provided a method for improving the melt viscosity of a linear polyester resin comprising compounding with a linear polyester resin an effective amount of a difunctional polyepoxy compound and an effective amount of a salt of an aliphatic carboxylic acid. Further, according to the present invention, there are provided articles made from the polyester compositions of the present invention.

DETAILED DESCRIPTION OF THE PRESENT INVENTION

Component (a) of the present invention comprises linear polyester resins. Polyesters generally for use herein are derived from an aliphatic or cycloaliphatic diol, or mixtures thereof, containing from 2 to about 10 carbon atoms and at least one aromatic dicarboxylic acid. Preferred polyesters are derived from an aliphatic diol and an aromatic dicarboxylic acid and have repeating units of the following general formula:

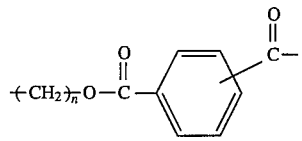

wherein n is an integer of from 2 to 6. The most preferred polyesters are poly (ethylene terephthalate), poly (1,4-butylene terephthalate) and mixtures thereof.

Also contemplated herein are the above polyesters with minor amounts, e.g., from 0.5 to about 5 percent by weight, of units derived from aliphatic acids and/or aliphatic polyols to form copolyesters. The aliphatic polyols include glycols, such as poly(ethylene glycol). All such polyesters can be made following the teachings of, for example, U.S. Pat. Nos. 2,465,319 and 3,047,539.

The polyesters which are derived from a cycloaliphatic diol and an aromatic dicarboxylic acid are prepared, for example, by condensing either the cis- or trans-isomer (or mixtures thereof) of, for example, 1,4-cyclohexanedimethanol with and aromatic dicarboxylic acid so as to produce a polyester having recurring units of the following formula:

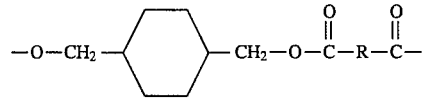

wherein the cyclohexane ring is selected form the cis- and trans-isomers thereof and R represents an aryl radical containing 6 to 20 carbon atoms and which is the decarboxylated residue derived from an aromatic dicarboxylic acid.

Examples of aromatic dicarboxylic acids represented by the decarboxylated residue R are isophthalic or terephthalic acid, 1,2-di-(p-carboxyphenyl)ethane, 4,4'-dicarboxydiphenyl ether, etc., and mixtures of these. All of these acids contain at least one aromatic nucleus. Acids containing fused rings can also be present, such as in 1,4- or 1,5-naphthalenedicarboxylic acids. The preferred dicarboxylic acids are terephthalic acid or a mixture of terephthalic and isophthalic acids.

Another preferred polyester may be derived from the reaction of either the cis- or trans-isomer (or a mixture thereof) of 1,4-cyclohexanedimethanol with a mixture of isophthalic and terephthalic acids. Such a polyester would have repeating units of the formula:

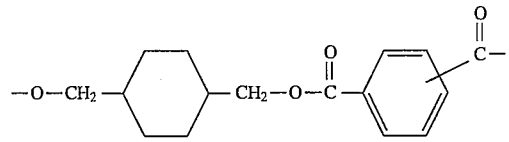

Still another preferred polyester is a copolyester derived from a cyclohexanedimethanol, an alkylene glycol and an aromatic dicarboxylic acid. These copolyesters are prepared by condensing either the cis- or trans-isomer (or mixture thereof) of, for example, 1,4-cyclohexanedimethanol and an alkylene glycol with an aromatic dicarboxylic acid so as to produce a copolyester having units of the formulae:

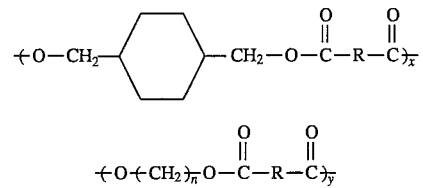

wherein the cyclohexane ring is selected from the cis- and trans-isomers thereof, R is as previously defined, n is an integer of 2 to 6, the x units comprise from about 10 to about 90 percent by weight and the y units comprise from about 90 to about 10 percent by weight.

Such a preferred copolyester may be derived from the reaction of either the cis- or trans-isomer (or mixtures thereof ) of 1,4-cyclohexanedimethanol and ethylene glycol with terephthalic acid in a molar ration of 1:2:3. These copolyesters have repeating units of the following formulae:

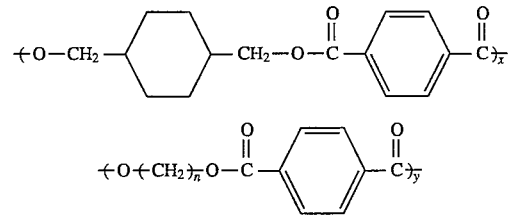

wherein x and y are as previously defined.

The polyesters described herein are either commercially available or can be produced by methods well known in the art, such as those set forth in, for example, U.S. Pat. No. 2,901,466.

The polyesters used herein have an intrinsic viscosity of from about 0.4 to about 2.0 dl/g as measured in a 60:40 phenol/tetrachloroethane mixture or similar solvent at 23°–30° C.

The polyester resin component can vary widely in amount. Preferably the polyester resin component is present in an amount ranging from about 60 to about 100 weight percent based on the total weight of the composition. More preferably the polyester resin component is present in an amount ranging from about 90 to about 100 weight percent based on the total weight of the composition. Where a blend of poly(ethylene terephthalate) and poly(1,4-butylene terephthalate) is employed, the polyester resin component will comprise from about 1 to about 99 parts by weight poly(ethylene terephthalate) and from about 99 to about 1 part by weight poly(1,4-butylene terephthalate) based on 100 parts by weight of the poly(ethylene terephthalate) and poly(1,4-butylene terephthalate) combined. However, other polyester blends are also contemplated within the scope of the present invention.

Component (b) is at least one difunctional epoxy compound. By difunctional epoxy compound is meant a compound having two terminal epoxy functionalities. Preferably the compound will contain only carbon, hydrogen and oxygen. The compound will preferably have a molecular weight of below about 1000, to facilitate blending with the polyester resin. Preferred difunctional epoxy compounds will have at least one of the epoxide groups on a cyclohexane ring. Examples of preferred difunctional epoxy compounds are 3,4-epoxycyclohexyl-3,4-epoxycyclohexylcarboxylate, bis(3,4-epoxycyclohexylmethyl) adipate, vinylcyclohexene di-epoxide, bisphenol diglycidyl ethers, diglycidyl adducts of amines and amides, diglycidyl adducts of carboxylic acids and the like. Especially preferred is 3,4-epoxycyclohexyl-3,4 epoxycyclohexylcarboxylate.

The difunctional epoxide compounds can be made by techniques well known to those skilled in the art. For example, the corresponding α,β-dihydroxy compounds can be dehydrated to produce the epoxide groups, or the correspondingly unsaturated compounds can be epoxidized by treatment with a peracid, such as peracetic acid, in well-known techniques. The compounds are also commercially available.

The difunctional epoxy compound may be employed in any effective amount, but preferably small amounts are use, e.g., at a range of about 0.1 to about 5 percent by weight. However, a particularly preferred range is from about 0.1 to about 3.5 percent by weight. A more preferred range is from about 0.5 to about 2 percent by weight. Within this particularly preferred range it has been found advantageous to employ in certain compositions from about 1 to about 1.5 percent by weight of the difunctional polyepoxy compound. All percentages are based on the combined weights of polyester component and the organic difunctional epoxide component.

Component (c) of the present invention consists of the catalyst compound. Preferred catalysts are salts free from direct carbon-phosphorous bonds and containing at least one of alkali metal cations and alkaline earth metal cations and halide anions. It is apparent that this class contains a large number of compounds. They include alkali metal halides, alkali metal carboxylates, alkali metal enolates, amine hydrohalides, alkali metal carbonates and quaternary ammonium halides. Illustrative compounds within this class are lithium fluoride, lithium iodide, potassium bromide, potassium iodide, sodium dihydrogen phosphate, sodium acetate, sodium benzoate, sodium caproate, sodium stearate, sodium ascorbate and dodecyltrimethylammonium bromide.

Salts of aliphatic carboxylic acids containing at least about 18 carbon atoms, especially the alkali metal stearates and preferably sodium stearate, have certain advantages over the other catalysts employed according to the invention and are therefore often preferred. In the first place, their use permits extrusion of the polyester-difunctional epoxide composition at substantially higher feed rates than those which are effective in their absence. In the second place, they tend to suppress the formation of acrolein, a by-product from glycidyl reagents. In the third place, they impart substantially less odor to the composition than certain other compounds useful as catalysts, especially amines.

The catalyst component can be present in the composition of the present invention in any effective amount. Preferably the catalyst is present in an amount ranging from about 0.01 to about 1 weight percent, more preferably from about 0.03 to about 0.1 weight percent based on the total weight of the resin composition.

Optionally, the present invention further comprises component (d) a hindered phenol thermal antioxidant. Any hindered phenol known to those skilled in the art may be employed herein, a wide variety of these are commercially available.

Hindered phenols will generally be of the type in which there is a sterically hindered phenolic group, especially one containing a t-butyl group in the ortho position to the phenolic OH group. Examples of such compounds are many. Preferred examples are, tetrakis (methylene-3-(-3',5'-di-tert-butyl-4'-hydroxyphenyl)-propionate) methane; octadecyl-3-(3',5'-di-tert-butyl-4'-hydroxyphenyl) propionate; 1,3,5-trimethyl-2,4,6-tris(3,5-di-tert-butyl-4-hydroxybenzyl)benzene; 4,4'-(2,2-diphenylpropyl)-diphenylamine; esters of ethoxylated aryl phenols; 2,2'-thiodiethylbis(3-(3,5-di-tert-butyl-4-hydroxyphenyl))propionate; octadecyl-3,5-di-tert-butyl-4-hydroxyhydrocinnamate and mixtures of any of the foregoing. Most preferred is octadecyl-3,5-di-tert-butyl-4-hydroxyhydrocinnamate, which is commercially available as "IRGANOX" 1076.

The compositions of the present invention can also comprise any number of conventional additives, such as dyes, pigments, stabilizers, plasticizers, reinforcers, flame retardants, drip retardants, nucleants, rubbery impact modifiers and the like. These are added, as desired, for their conventionally employed purposes. Illustrative flame retardant additives are disclosed in U.S. Pat. Nos. 3,833,685; 3,342,254; 3,915,926 and 3,671,487. Other flame retardants are disclosed in U.S. Pat. Nos. 3,681,281; 3,557,053; 3,830,771 and United Kingdom Pat. No. 1,358,080.

Generally speaking, the more important of the flame retardant compounds contain chemical elements employed for their ability to impart flame resistance, e.g., bromine, chlorine, antimony, phosphorous and nitrogen. It is preferred that the flame-retardant additive comprise a halogenated organic compound (brominated or chlorinated); a halogenated-containing organic compound in admixture with a phosphorous compound or compounds containing phosphorous-nitrogen bonds or a mixture of two or more of the foregoing.

The amount of flame retardant additive used is not critical to the present invention, so long as it is present in minor proportion based on said composition, major proportions will detract from physical properties, but at least sufficient to render the polyester resin non-burning or self-extinguishing. Those skilled in the art are well aware that the amount will vary with the nature of the resin and with the efficiency of the additive. In general, however, the amount of the additive will be from 0.5 to 50 parts by weight per 100 parts of resin.

A preferred range will be from about 3 to about 25 parts and an especially preferred range will be from about 8 to about 12 parts of flame retardant additive per 100 parts of resin. Smaller amounts of compounds highly concentrated in the elements responsible for flame-retardance will be sufficient, e.g., elemental red phosphorous will be preferred at 0.5 to 2.0 parts by weight per hundred parts of resin, while phosphorous in the form of triphenyl phosphate will be used at 25 parts of phosphate per 100 parts of resin, and so forth. Halogenated aromatics will be used at 8 to 12 parts and synergists, e.g., antimony oxide, will be used at about 2 to about 5 parts by weight per 100 parts by weight of resin.

The compositions of the present invention may also comprise a drip retardant agent. These are described in U.S. Pat. No. 3,671,487. Generally, the drip retardant agent comprises a polytetrafluoroethylene resin, which is commercially available or can be prepared by known processes. They are white solids obtained by polymerization of the tetrafluoroethylene in aqueous media with free radical catalysts, e.g., sodium, potassium or ammonium peroxydisulfates at 100 to 1,000 psi and at 0°–200° C. and preferably 20°–100° C. See, Brubaker, U.S. Pat. No. 2,393,967.

Preferred among the reinforcing agents are minerals such as mica, asbestos, wollastonite, clay, talc, carbon, ceramic, titanate, and mixtures thereof. Talc is especially preferred.

A most preferred reinforcing agent comprises glass fillers. Preferably the glass fillers are in the form of filamentous glass fibers or glass flakes. These are well known to those skilled in the art and are widely available from a number of manufacturers. For compositions ultimately employed for electrical uses, it is preferred to use fibrous glass filaments comprised of lime-aluminum borosilicate glass that is relatively sodium free. This is known as "E" glass. However, other glass compositions are useful. Especially preferred are K filament glass (about 14 micron diameter), G filament glass (about 10 micron diameter) and D filament glass (about 7 micron diameter). All such glasses are contemplated as within the scope of the present invention. The filaments are made by standard processes, e.g., by steam or air blowing, flame blowing and mechanical pulling. The preferred filaments for plastics reinforcement are made by mechanical pulling. The filament diameters preferably range from about 0.00012 to about 0.00075 inch, but this is not critical to the present invention. It is known, however, to those skilled in the art, that smaller filament diameters will also increase the strength of plastics treated therewith.

The length of the glass filaments and whether or not they are bundled into fibers and the fibers bundled in turn to yarns, ropes or rovings, or woven into mats, and the like are also not critical to the invention. However, in preparing the molding compositions of the present invention, it is convenient to use filamentous glass in the form of chopped strands of from about one-eighth to about 2 inches long. In articles molded from the compositions, on the other hand, even shorter lengths will be encountered because, during compounding, considerable fragmentation will occur.

The process of this invention can be carried out by a number of procedures. In one way, the difunctional epoxide compound is put into an extrusion compounder with the dry polyester and salt of an aliphatic carboxylic acid, and the blend is heated at an elevated temperature, e.g., 450°–550° F., and extruded to produce molding pellets. The difunctional epoxide compound is dispersed in the polyester resin and catalyst, and the melt viscosity is elevated in the process. In another procedure, the difunctional epoxide compound is mixed with the polyester resin and catalyst blending at ordinary temperatures, then the blend is fluxed on a mill, heated, e.g. at 450°–550° F., cooled and chopped. The difunctional epoxide compound can also be mixed with the powdered or granular polyester and the catalyst, and the mixture can be heated and directly formed into molded items using machines which compound and mold. In still another procedure, the difunctional epoxide compound may be incorporated in the final stage of the polyester resin manufacture process.

Compounding should be carried out to ensure that the temperature is carefully controlled; and is preferably maintained below about 530° F. Preferably the compounding is continued until an intimate blend between the resin, the catalyst and difunctional epoxide compound is obtained.

The other above-mentioned additives can be added during compounding to impart on the blend the desired characteristics, as known to those skilled in the art.

The compositions of the present invention may then be formed into various articles. Preferably the compounded resin is extruded into a sheet and then thermoformed into a variety of articles or is extruded into a tube. The compositions are also suitable for profile extrusion, molding and other processes known to those skilled in the art that require higher melt strength than normal systems. See, e.g. *Modern Plastics Encyclopedia '89*, McGraw Hill, Vol. 65, No. 11, pp. 215–308.

A particularly preferred article is a core tube which covers fibers in buffer tubes and which is prepared from a polyester composition comprised of a polyester resin, a difunctional epoxide compound and a catalyst.

DESCRIPTION OF THE PREFERRED EMBODIMENTS

The following specific examples illustrate the present invention. However, they are not to be construed to limit the claims in any manner whatsoever.

EXAMPLES 1–3

Polyester compositions are prepared by tumble blending the respective ingredients and compounding in a 2.5∴ vacuum vented Prodex single screw extruder. The extruder parameters were : 480° F. barrel set temperature, 100–110 rpm screw speed, and approximately 600 g/min feedrate. After drying at 120° C. for four hours, the blends were injected molded into test specimens using a 480° F. barrel set temperature, 140° F. mold temperature, 11 second injection time, 15 second hold time, and 200 psi back pressure.

The tensile properties of the test specimens were determined on a Type V tensile bars (2.5×0.125 inch) using a 0.5 inch/min crosshead speed. Percent elongation was measured by crosshead displacement at break. Tensile strength is reported in psi.

The samples were further aged for hydrolysis testing. Aging was accomplished by suspending the samples in a closed container over a saturated aqueous potassium sulfate solution held at 94% relative humidity and 85° C. After exposure, the samples were removed and held at ambient conditions for at least 24 hours.

Melt viscosities of the blends were measured on a Tinius Olsen Melt Indexer. The resin blends were extruded with a 21,500 g load through a 0.0425 inch orifice at 480° F.

For comparative purposes, samples were prepared without addition of difunctional epoxide compound and catalyst.

The results along with the resin blend compositions are reported below in Table 1.

TABLE 1

| Example | A* | 1 | 2 | 3 |
|---|---|---|---|---|
| Composition | | | | |
| Polyester[a], wt. % | 100 | 99 | 99 | 98.5 |
| Diepoxide[b], wt. % | — | 1 | 1 | 1.5 |
| Catalyst[c], phr | — | 0.025 | 0.05 | 0.05 |
| Properties | | | | |
| TE[d] as molded | 378 | 228 | 284 | 250 |

TABLE 1-continued

| Example | A* | 1 | 2 | 3 |
|---|---|---|---|---|
| TS[e] as molded | 7307 | 7126 | 6988 | 7058 |
| TE aged 1 day | 341 | 217 | 264 | 274 |
| TS aged 1 day | 7428 | 7354 | 7265 | 7340 |
| TE aged 3 weeks | 119 | 99 | 249 | 97 |
| TS aged 3 weeks | 8352 | 7674 | 7560 | 7556 |
| TE aged 4 weeks | 93 | 178 | 223 | 253 |
| TS aged 4 weeks | 8329 | 7607 | 7581 | 7287 |
| Melt Viscosity, poise | | | | |
| Pellets | 7497 | 25657 | 28460 | 13783 |
| As molded | 6068 | 27150 | 28004 | 11940 |
| Aged 4 weeks | 686 | 13073 | 20880 | 9353 |

*= Comparative example
phr = parts per hundred
[a]= Poly(1,4-butylene terephthalate), "VALOX" 315, General Electric Company
[b]= 3,4-epoxycyclohexylmethyl-3,4-epoxycyclohexylcarboxylate, "BAKELITE" ERL 4221, Union Carbide Company
[c]= Sodium stearate
[d]= Tensile elongation, %
[e]= Tensile strength, psi As is clearly demonstrated by Table 1 above, the polyester compositions having the difunctional epoxy compound and catalyst exhibit vastly superior melt viscosity and tensile elongation properties after aging over the polyester resin alone.

EXAMPLES 4–5

The procedure of Examples 1–3 is followed except the blends are compounded in a 30 mm Werner Pfleiderer twin screw extruder at a 480° F. barrel set temperature, screw speed of 300 rpm and a feedrate of 250–320 g/min. The results, along with compositional data are set forth below in Table 2.

TABLE 2

| Example | B* | C* | 4 | 5 |
|---|---|---|---|---|
| Composition | | | | |
| Polyester[a], wt. % | 100 | 99 | 99 | 99 |
| Diepoxy[b], wt. % | — | 1 | 1 | 1 |
| Catalyst[c], phr | — | — | 0.05 | 0.1 |
| Properties | | | | |
| Tensile Elongation | | | | |
| As molded | 272 | 348 | 261 | 267 |
| Aged 1 day | 223 | 236 | 231 | 244 |
| Aged 3 weeks | 137 | 140 | 247 | 175 |
| Aged 4 weeks | 50 | 172 | 254 | 203 |
| Aged 5 weeks | 9 | 160 | 258 | 177 |
| Aged 6 weeks | 4 | 147 | 272 | 182 |
| Melt Viscosity, poise | | | | |
| As molded | 3147 | 3900 | 7500 | 7161 |
| Aged 1 day | 2927 | 3366 | 7372 | 7145 |
| Aged 3 weeks | 1247 | 1482 | 6717 | 6315 |
| Aged 4 weeks | — | — | 6230 | 5839 |
| Aged 6 weeks | 133 | — | 6152 | 5665 |

*= Comparative Example
phr = parts per hundred
[a]= Poly(1,4-butylene terephthalate), "VALOX", 5611 poise General Electric Company
[b]= 3,4-epoxycyclohexylmethyl-3,4-epoxycyclohexylcarboxylate, "BAKELITE" ERL 4221, Union Carbide Company
[c]= Sodium stearate As can clearly be seen from Table 2 above, the polyester composition melt blended with the difunctional epoxy compound and catalyst exhibited significantly better melt viscosity and tensile elongation retention after aging than did the polyester alone or the polyester melt blended with the difunctional epoxy compound only.

EXAMPLES 6–7

The procedure of Examples 1–3 is followed, except comparison is made with polyester resins blended with monofunctional epoxide compounds. The formulations are prepared so that an equivalent number of epoxide groups are introduced in each case.

The samples were aged by suspending the samples above the water level in a pressure steam sterilizer, Model No. 25x, Wisconsin Aluminum Foundry Company, at 100% relative humidity, 110° C., and at a pressure of 0.4 kg/cm$^2$. After exposure, the samples were removed and held at ambient conditions for at least 24 hours.

The results, along with compositional data are reported below in Table 3.

TABLE 3

| Example | D* | E* | 5 | 6 |
|---|---|---|---|---|
| Composition | | | | |
| Polyester[a], wt. % | 100 | 100 | 100 | 100 |
| Epoxide, phr | 3.1[c] | — | 1.5 | 1.5[b] |
| Catalyst, phr | 0.06[d] | — | 0.06[d] | 0.05[e] |
| Properties | | | | |
| Melt viscosity, poise | 4801 | 5442 | 18531 | 13976 |
| TE as molded | 325 | 202 | 264 | 198 |
| TS as molded | 6953 | 8078 | 7730 | 7717 |
| TE aged 1 day | 264 | 92 | 202 | 206 |
| TS aged 1 day | 7267 | 8070 | 7251 | 7143 |
| TE aged 3 days | 194 | 20 | 220 | 165 |
| TS aged 3 days | 7209 | 8548 | 7327 | 7230 |
| TE aged 5 days | 63 | 4 | 220 | 185 |
| TS aged 5 days | 7486 | 3993 | 7378 | 7183 |
| TE aged 7 days | 17 | A | 156 | 169 |
| TS aged 7 days | 8013 | A | 7533 | 7321 |

*= Comparative Example
phr = parts per hundred
[a]= Poly(1,4-butylene terephthalite), "VALOX" 315, General Electric Company
[b]= 3,4-epoxycyclohexylmethyl-3,4-epoxycyclohexylcarboxylate, "BAKELITE"ERL 4221, Union Carbide Company
[c]= aliphatic glycidyl ether, "EPODIL" 748, Pacific Anchor Chemical Company
[d]= sodium stearate
[e]= potassium iodide
A = too brittle to test From Table 3 above it can clearly be seen that polyester compositions compounded with difunctional epoxy compounds have much improved melt viscosity stability over polyester compositions compounded with monofunctional epoxy compounds. Further, it can be seen that much larger quantities of monofunctional epoxide compound are necessary to achieve some improvement in melt stability compared to the difunctional epoxy compounds. Table 3 also shows that metal halides are useful catalysts for the compositions of the present invention.

EXAMPLES 7–8

The procedure of Examples 1–3 is followed except that comparison is made between the diepoxy compounds of the present invention and a trifunctional epoxide. The formulations are prepared so that an equivalent number of epoxide groups are introduced in each case. Aging was performed employing the 110° C./100% relative humidity exposure environment. Results, along with compositional data are reported below in Table 4.

TABLE 4

| Examples | F* | G* | 7 | 8 |
|---|---|---|---|---|
| Composition | | | | |
| Polyester[a], wt. % | 100 | 100 | 100 | 100 |
| ERL 4221[b], phr | — | — | 1.3 | 0.64 |
| TGIC[c], phr | 1.0 | 0.5 | — | — |
| Na Stearate, phr | 0.065 | 0.065 | 0.065 | 0.065 |
| Hindered Phenol[d], phr | 0.2 | 0.2 | 0.2 | 0.2 |
| Properties | | | | |
| Melt viscosity, poise | | | | |
| As molded | 26558 | 13725 | 19092 | 14245 |
| Aged 3 days | 1173 | 734 | 12343 | 2993 |

*= Comparative Example
phr = parts per hundred
[a]= Poly(1,4-butylene terephthalate), "VALOX" 315, General Electric Company
[b]= 3,4-epoxycyclohexylmethyl-3,4-epoxycyclohexylcarboxylate, "BAKELITE", Union Carbide Company
[c]= Triglycidyl isocyanurate
[d]= "IRGANOX" 1076, Ciba Geigy Company As can be clearly seen from Table 4 above, the polyester composition compounded with a difunctional epoxy compound exhibits significantly improved retention of melt viscosity after aging, than does the polyester resin treated with an equivalent number of epoxy groups from the trifunctional epoxy compound.

EXAMPLES 9–14

The procedure of Examples 1–3 was followed except that the amount of ERL 4221 employed is varied. The results, along with compositional data, are set forth below in Table 5. A control example employing the polyester without the difunctional epoxide and catalyst is also shown.

TABLE 5

| Examples | H* | 9 | 10 | 11 | 12 | 13 | 14 |
|---|---|---|---|---|---|---|---|
| Composition, phw | | | | | | | |
| Polyester[a] | 100 | 100 | 100 | 100 | 100 | 100 | 100 |
| ERL 4221[b] | — | 0.2 | 0.6 | 0.8 | 1.0 | 1.5 | 2.0 |
| Na Stearate | — | 0.05 | 0.05 | 0.05 | 0.05 | 0.05 | 0.05 |
| Irganox[c] | 0.1 | 0.1 | 0.1 | 0.1 | 0.1 | 0.1 | 0.1 |
| Properties | | | | | | | |
| Melt Viscosity, poise | | | | | | | |
| As molded | 4194 | 9603 | 15601 | 18884 | 20336 | 13188 | 7395 |
| Aged 3 weeks | — | 2072 | 5995 | 12253 | 19782 | — | — |
| Aged 5 weeks | 510 | — | — | — | — | — | — |
| Aged 6 weeks | — | 307 | 1048 | 3081 | 8784 | 8409 | 5147 |
| Tensile | | | | | | | |
| TE as molded | 275 | 158 | 271 | 264 | 259 | 267 | 256 |
| TS as molded | 7838 | 7684 | 7458 | 7417 | 7394 | 7454 | 7314 |
| TE aged 1 day | 205 | 285 | 263 | 272 | 257 | 243 | 201 |
| TS aged 1 day | 8422 | 7662 | 7499 | 7494 | 7478 | 7331 | 7019 |
| TE aged 3 weeks | 113 | 177 | 256 | 271 | 249 | 239 | 110 |
| TS aged 3 weeks | 8079 | 7800 | 7492 | 7324 | 7310 | 7685 | 7529 |
| TE aged 6 weeks | 11 | 7 | 131 | 166 | 255 | 173 | 251 |
| TS aged 6 weeks | 8552 | 8263 | 8184 | 7881 | 7575 | 7536 | 7467 |

*= Control example
pbw = parts by weight
[a]= "VALOX" 315, poly(1,4-butylene terephthalate), General Electric Company
[b]= 3,4-epoxycyclohexylmethyl-3,4-epoxycyclohexylcarboxylate, "BAKELITE", Union Carbide Co.
[c]= hindered phenol antioxidant, Ciba Geigy Company Table 5 above clearly shows that polyester compositions having excellent melt viscosity properties can be obtained with a wide range of difunctional epoxy compound concentrations. Surprisingly, polyester compositions having the highest melt viscosity are obtained at difunctional epoxy compound concentrations of from 0.6 to 1.5 weight percent.

The above-mentioned patents and patent applications are all hereby incorporated by reference.

Many variations of the present invention will suggest themselves to those skilled in this art in light of the above detailed description. For example, instead of poly(1,4-butylene terephthalate), other polyester resins such as a poly(ethylene terephthalate), a poly(1,4-cyclohexanedimethanol terephthalate) or mixtures thereof may be employed. Additionally, a number of other difunctional epoxide compounds may be effectively employed, such as vinylcyclohexene di-epoxide, bis(3,4-epoxycyclohexylmethyl) adipate, or mixtures thereof. It is also within the scope of the instant invention to employ a monofunctional epoxy compound in combination with the difunctional epoxy compound. Also contemplated for use herein as a catalyst compound are potassium bromide, lithium iodide, lithium fluoride, sodium acetate, potassium iodide, sodium caproate, sodium benzoate, sodium ascorbate, sodium dihydrogen phosphate, and mixtures thereof. It is further contemplated to add to the polyester compositions any of the known hindered phenols, as well as a wide variety of conventional additives including, but not limited to, flame and drip retardants. It is further within the scope of the present invention to modify the compositions of the present invention with reinforcing agents, epsecially glass fibers and glass flakes. All such obvious modifications are within the full intended scope of the appended claims.

We claim:

1. A thermoplastic resin composition, comprising:
   (a) a linear polyester resin;
   (b) an effective amount of at least one difunctional epoxy compound, said at least one difunctional epoxy compound having at least one cyclohexane ring moiety and having two terminal epoxy functional groups, wherein at least one of the two terminal epoxy functional groups is a substituent on the at least one cyclohexane ring moiety; and
   (c) an effective amount of a catalyst compound;
wherein the amounts of components (b) and (c) are effective to provide improved melt viscosity stability.

2. A composition as defined in claim 1 wherein said component (a) polyester resin comprises units of an aliphatic diol, a cycloaliphatic diol or a mixture of such diols and an aromatic diacid.

3. A composition as defined in claim 2 wherein said component (a) is selected from the group consisting of a poly(1,4-butylene terephthalate), poly(ethylene terephthalate), poly(1,4-cyclohexanedimethanol terephthalate) and blends of any of the foregoing.

4. A composition as defined in claim 3 wherein said component (a) comprises poly(1,4-butylene terephthalate).

5. A composition as defined in claim 1 wherein said component (a) polyester resin has an intrinsic viscosity of at least about 0.4 deciliters per gram when measured in a 60:40 mixture of phenol and trichloroethane at 25° C.

6. A composition as defined in claim 1 wherein said at least one difunctional epoxy compound is selected from the group consisting of bis(3,4-epoxycyclohexylmethyl) adipate; vinylcyclohexene diepoxide; 3,4-epoxycyclohexl-3,4-epoxycyclohexcarboxylate; 3,4-epoxycyclohexylmethyl-3,4-epoxycyclohexlcarboxylate and mixtures of any of the foregoing.

7. A composition as defined in claim 6 wherein said difunctional epoxy compound comprises 3,4-epoxycyclohexylmethyl-3,4-epoxycyclohexlcarboxylate.

8. A composition as defined in claim 1 wherein said catalyst compound (c) comprises a salt free from direct carbon-phosphorous bonds and containing at least one of alkali metal cations and alkaline earth metal cations and halide anions.

9. A composition as defined in claim 8 wherein said catalyst compound (c) is selected from the group consisting of potassium bromide, potassium iodide, lithium iodide, lithium fluoride, sodium acetate, sodium caproate, sodium benzoate, sodium stearate, sodium ascorbate, sodium dihydrogen phosphate, dodecyltrimethylammonium bromide and mixtures thereof.

10. A composition as defined in claim 9 wherein said catalyst component comprises sodium stearate.

11. A composition as defined in claim 1 wherein said composition further comprises:
   (d) a hindered phenol antioxidant.

12. A composition as defined in claim 1 wherein said composition further comprises an additive selected from the group consisting of flame retardants, drip retardants, reinforcers, dyes, pigments, stabilizers, nucleants, rubbery impact modifiers and mixtures of any of the foregoing.

13. A composition as defined in claim 1 wherein said difunctional epoxy compound is present in an amount ranging from about 0.1 to about 3.5 weight percent based on the total weight of the composition.

14. A composition as defined in claim 13 wherein said difunctional epoxy compound is present in an amount ranging from about 0.5 to about 2 weight percent based on the total weight of the composition.

15. A composition as defined in claim 14 wherein said difunctional epoxy compound is present in an amount ranging from about 1 to about 1.5 weight percent based on the total weight of the composition.

16. A composition as defined in claim 1 wherein said catalyst compound is present in an amount ranging from about 0.01 to about 1 weight percent based on the total weight of the composition.

17. A composition as defined in claim 16 wherein said catalyst compound is present in an amount ranging from about 0.03 to about 0.1 weight percent based on the total weight of the composition.

18. A method for improving the hydrolytic stability of a thermoplastic linear polyester composition comprising compounding:
   (a) a linear polyester resin;
   (b) from 0.1 percent by weight to 5 percent by weight of at least one difunctional epoxy compound, said at least one difunctional epoxy compound having at least one cyclohexane ring moiety and having two terminal epoxy functional groups, wherein at least one of the two terminal epoxy functional groups is a substituent on the at least one cyclohexane ring moiety and wherein the amount of difunctional epoxy compound is based on the combined weights of the linear polyester resin and difunctional epoxy compound; and
   (c) from 0.01 percent by weight to 1 percent by weight of a catalyst, wherein the amount of catalyst is based on the total weight of the resin composition.

19. A method as defined in claim 18 wherein said polyester resin comprises units of an aliphatic diol, a cycloaliphatic diol or a mixture of such diols and an aromatic diacid.

20. A method as defined in claim 17 wherein said polyester resin is selected from the group consisting of poly(1,4-butylene terephthalate), a poly(1,4-cyclohexanedimethanol terephthalate), a poly)ethylene terephthalate), and blends of any of the foregoing.

21. A method as defined in claim 20 wherein said polyester resin comprises a poly(1,4-butylene terephthalate).

22. A method as defined in claim 18 wherein said polyester resin has an intrinsic viscosity of at least about 0.4 deciliters per gram when measured in a 60:40 mixture of phenol and trichloroethane at 25° C.

23. A method as defined in claim 18 wherein said at least one difunctional epoxy compound is selected from the group consisting of bis(3,4-epoxycyclohexylmethyl)adipate; vinylcyclohexene diepoxide; 3,4-epoxycyclohexylmethyl-3,4-epoxycyclohexlcarboxylate; 3,4-epoxycyclohexylmethyl-3,4-epoxycyclohexlcarboxylate and mixtures of any of the foregoing.

24. A method as defined in claim 23 wherein said difunctional epoxy compound comprises 3,4-epoxycyclohexylmethyl-3,4-epoxycyclohexylcarboxylate.

25. A method as defined in claim 18 wherein said catalyst compound comprises salts free from direct carbon-phosphorous bonds and containing at least one of alkali metal cations and alkaline earth metal cations and halide ions.

26. A method as defined in claim 25 wherein said catalyst compound is selected from the group consisting of potassium bromide, potassium iodide, lithium iodide, lithium fluoride, sodium acetate, sodium caproate, sodium benzoate, sodium stearate, sodium ascorbate, sodium dihydrogen phosphate, dodecyltrimethylammonium bromide and mixtures thereof.

27. A method as defined in claim 26 wherein said catalyst compound comprises sodium stearate.

28. A method as defined in claim 18 wherein said method further comprises compounding into the composition a hindered phenol antioxidant.

29. A method as defined in claim 18 wherein said method further comprises compounding into the composition an additive selected from the group consisting of flame retardants, drip retardants, dyes, pigments, stabilizers, plasticizers, nucleants, reinforcers, rubbery impact modifiers and mixtures of any of the foregoing.

30. A method as defined in claim 18 wherein said compounding comprises melt blending or milling.

31. A method as defined in claim 18 wherein said effective amount of a difunctional epoxy compound comprises from about 0.1 to about 3.5 weight percent based on the total weight of the compounded composition.

32. A method as defined in claim 31 wherein said effective amount of a difunctional epoxy compound comprises from about 0.5 to about 2 weight percent based on the total weight of the compounded composition.

33. A method as defined in claim 32 wherein said effective amount of a difunctional epoxy compound comprises from about 1 to about 1.5 weight percent based on the total weight of the compounded composition.

34. A method as defined in claim 33 wherein said effective amount of a catalyst compound comprises from about 0.01 to about 1 weight percent based on the total weight of the compounded composition.

35. A method as defined in claim 34 wherein said effective amount of a catalyst compound comprises from about 0.03 to about 0.1 weight percent based on the total weight of the compounded composition.

36. A method for making an article, comprising:

extruding and thermoforming, extruding or molding the composition as defined in claim 1.

37. An article made by the process of claim 36.

38. An article according to claim 37, wherein the article comprises a tube.

39. The reaction product of claim 18.

* * * * *